United States Patent [19]
Williams

[11] Patent Number: 6,140,535
[45] Date of Patent: *Oct. 31, 2000

[54] IRIDIUM-CATALYZED CARBONYLATION PROCESS FOR THE PRODUCTION OF ACETIC ACID

[75] Inventor: Bruce L Williams, Elloughton Brough, United Kingdom

[73] Assignee: BP Chemicals Limited, London, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/992,105

[22] Filed: Dec. 17, 1997

[30] Foreign Application Priority Data

Dec. 19, 1996 [GB] United Kingdom .................. 9626324

[51] Int. Cl.$^7$ .......................... C07C 51/12; C07C 51/14; C07C 51/42
[52] U.S. Cl. .......................... 562/519; 562/520; 562/608
[58] Field of Search ...................... 562/519, 520, 562/608

[56] References Cited

U.S. PATENT DOCUMENTS

| | | | |
|---|---|---|---|
| 3,769,177 | 10/1973 | Eubanks et al. | 203/71 |
| 3,769,329 | 10/1973 | Paulik et al. | 260/488 K |
| 3,772,156 | 11/1973 | Johnson et al. | 203/33 |
| 3,791,935 | 2/1974 | Eubanks et al. | 203/74 |
| 4,008,131 | 2/1977 | Price | 203/82 |
| 4,029,553 | 6/1977 | Price | 203/94 |
| 4,039,395 | 8/1977 | Eby | 203/38 |
| 5,672,743 | 9/1997 | Garland et al. | 562/519 |
| 5,877,348 | 3/1999 | Ditzel et al. | 562/519 |

FOREIGN PATENT DOCUMENTS

| | | |
|---|---|---|
| 0 573 189 A1 | 12/1993 | European Pat. Off. . |
| 0 616 997 A1 | 9/1994 | European Pat. Off. . |
| 0 618 184 | 10/1994 | European Pat. Off. . |
| 0 643 034 A1 | 3/1995 | European Pat. Off. . |
| 0 752 406 A1 | 1/1997 | European Pat. Off. . |
| 1294432 | 10/1972 | United Kingdom . |
| 1343955 | 1/1974 | United Kingdom . |
| 1505336 | 3/1978 | United Kingdom . |
| 96/33965 | 10/1996 | WIPO . |

OTHER PUBLICATIONS

Howard et al, "C$_1$ to acetyls: catalysis and process," Catalysis Today, vol. 18, pp. 325–354 (1993). No month provided.

Cornils et al, "Applied Homogeneous Catalysis with Organometallic Compounds," vol. 1, pp. 104–138 (1996). No month provided.

Eby et al, "Methanol Carbonylation to Acetic Acid," Applied Industrial Catalysis, vol. 1, pp. 275–296 (1983). No month provided.

*Primary Examiner*—Samuel Barts
*Assistant Examiner*—Rosalynd Keys
*Attorney, Agent, or Firm*—Nixon & Vanderhye

[57] ABSTRACT

A process as provided for producing an acetic acid process stream having less than 400 ppm propionic acid and less than 1500 ppm water. Methanol or a reactive derivative thereof and carbon monoxide is fed to a carbonylation reactor in which there is maintained during the course of the process a liquid reaction composition containing an iridium carbonylation catalyst, methyl iodide co-catalyst, a promoter, water at a concentration of less than about 8% by weight, methyl acetate, acetic acid, and propionic acid by-product and its precursors. Liquid reaction composition is withdrawn from the carbonylation reactor and introduced to a flash zone to form a vapor fraction comprising water, acetic acid product, propionic acid by-product, methyl acetate, methyl iodide and propionic acid precursors, and a liquid fraction comprising involatile iridium catalyst, involatile optional promoter or promoters, acetic acid and water. The liquid fraction is recycled from the flash zone to the carbonylation reactor and introduced into a first distillation zone where a light ends recycle stream is removed and recycled to the carbonylation reactor, A process stream is removed from the first distillation zone comprising acetic acid, propionic acid by-product and less than 1500 ppm water. If the process stream comprises greater than 400 ppm propionic acid, the process stream is introduced into a second distillation zone where propionic acid by-product is removed together with an acetic acid process stream containing less than 400 ppm propionic acid and less than 1500 ppm water.

16 Claims, 3 Drawing Sheets

IRIDIUM-CATALYZED CARBONYLATION PROCESS FOR THE PRODUCTION OF ACETIC ACID

The present invention relates to a process for the production of acetic acid and in particular to a process for the production of acetic acid by the carbonylation of methanol and/or a reactive derivative thereof in the presence of an iridium catalyst.

Acetic acid is a well-known commodity chemical which has many industrial uses.

Processes for the production of acetic acid by liquid phase iridium-catalyzed carbonylation reactions are known and are described in for example, EP-A-0616997, EP-A-06 18184; EP-A-0643034; U.S. Pat. No. 3,772,380; GB-A-1234641 and (GB-A-1234642.

The construction and operation of carbonylation plant for the production of acetic acid is a competitive business and clearly any saving, in capital expenditure and operating costs by eliminating, plant is an economically desirable objective. The technical problem to be overcome by the process of the present invention is that of reducing the capital expenditure and/or operating costs of a plant for the production of acetic acid by the liquid phase carbonylation of methanol and/or a reactive derivative thereof using, an iridium catalyst. We have found that by operating with a defined liquid reaction composition it is possible to produce acetic acid of a quality sufficient in terms of water and propionic acid content for its ultimate industrial applications using a single distillation column to separate and recycle the light ends from the acetic acid product.

Accordingly,y the present invention provides a process for the production of an acetic acid process stream comprising less than 400 ppm propionic acid and less than 1500 ppm water which process comprises the steps:

(a) feeding methanol and/or a reactive derivative thereof and carbon monoxide to a carbonylation reactor in which there is maintained during the course of the process a liquid reaction composition comprising:
   (i) an iridium carbonylation catalyst;
   (ii) methyl iodide co-catalyst;
   (iii) optionally one or more promoters selected from the group consisting of ruthenium, osmium, rhenium, cadmium, mercury, zinc, gallium, indium and tungsten;
   (iv) a finite amount of water at a concentration of less than about 8% by weight;
   (v) methyl acetate;
   (vi) acetic acid; and
   (vii) propionic acid by-product and its precursors;

(b) withdrawing liquid reaction composition from the carbonylation reactor and introducing at least part of the withdrawn liquid reaction composition, with or without the addition of heat, to a flash zone to form a vapour fraction comprising water, acetic acid product, propionic acid by-product, methyl acetate, methyl iodide and propionic acid precursors, and a liquid fraction comprising involatile iridium catalyst, involatile optional promoter or promoters, acetic acid and water;

(c) recycling the liquid fraction from the flash zone to the carbonylation reactor;

(d) introducing the vapour fraction from the flash zone into a first distillation zone;

(e) removing from the first distillation zone at a point above the introduction point of the flash zone vapour fraction a light ends recycle stream comprising water, methyl acetate, methyl iodide, acetic acid and propionic acid precursors which stream is recycled in whole or in part to the carbonylation reactor, and (f) removing from the first distillation zone at a point below the introduction point of the flash zone vapour fraction, a process stream comprising acetic acid product, propionic acid by-product, and less than 1500 ppm water and, (g) if the process stream removed in step (f) comprises greater than 400 ppm propionic acid introducing, said stream into a second distillation column, removing from a point below the introduction point of the stream from (f) propionic acid by-product and from a point above the introduction point of the stream from (f) an acetic acid process stream containing less than 400 ppm propionic acid and less than 1500 ppm water.

Advantageously, the process of the invention allows the production of acetic acid containing less than 400 ppm , for example less than 300 ppm propionic acid and less than 1500 ppm water, for example less than 1000 ppm, using two or less distillation zones for the basic purification rather than the three generally employed in carbonylation purification systems.

Suitably, hydrogen present in the carbonylation reactor, present for example, as a result of the water gas shift reaction and optionally as part of the gas feed, is maintained at as low a partial pressure as possible, typically a partial pressure of less than 0.5 bar, preferably less than 0.3 bar. By maintaining as low a partial pressure of hydrogen as possible in the carbonylation reactor the amount of hydrogenation by-products (methane and propionic acid) is reduced. Preferably, hydrogen in the carbon monoxide feed gas is maintained at less than 0.5 mol %, more preferably less than 0.3 mol % and most preferably less than 0.1 mol %.

Suitably, the concentration of methyl iodide co-catalyst in the liquid reaction composition is greater than 4% by weight, typically from 4 to 20% by weight, preferably from 4 to 16% by weight. As the methyl iodide concentration in the liquid reaction composition is increased, the amount of propionic acid by-product decreases.

Suitably, the molar ratio of methyl iodide: iridium in the liquid reaction composition is [greater than 20]:1, preferably [up to 400]:1, more preferably [from 20 to 200]:1. As the molar ratio of methyl iodide: iridium catalyst in the liquid reaction composition is increased, the amount of propionic acid by-product decreases.

The flash zone is preferably maintained at a pressure below that of the reactor, typically at a pressure of 0 to 10 barg. The flash zone is preferably maintained at a temperature of 100 to 160° C.

The vapour fraction from the flash zone may be introduced to the first distillation zone as a vapour or the condensable components therein may be partially or fully condensed and the vapour fraction may be introduced as a mixed vapour/liquid or as a liquid with non-condensables.

The first distillation zone preferably has up to 40 theoretical stages. Since distillation zones may have differing efficiencies this may be equivalent to 57 actual stages with an efficiency of about 0.7 or 80 actual stages with an efficiency of about 0.5.

Preferably, the product acid stream may be removed at the base of the first distillation zone or at a point one or more stages above the base of the distillation zone. The process stream containing acetic acid may be withdrawn as a liquid or as a vapour. When the process stream is withdrawn as a vapour, preferably a small liquid bleed is also taken from the base of the distillation zone.

It will often be the case that the vapour stream passing overhead from the first distillation zone will be two phase when it is cooled. When the overhead stream is two phase it is preferred that the reflux to the distillation zone be provided by separating the phases and using only the light, aqueous phase; the heavy, methyl iodide-rich phase being recycled to the carbonylation reactor. At least a portion of the aqueous phase may be recycled to the carbonylation reactor.

In the process of the present invention, suitable reactive derivatives of methanol include methyl acetate, dimethyl ether and methyl iodide. A mixture of methanol and reactive derivatives thereof may be used as reactants in the process of the present invention. Preferably, methanol and/or methyl acetate are used as reactants. If methyl acetate or dimethyl ether are used water co-reactant is also required to produce acetic acid. At least some of the methanol and/or reactive derivative thereof will be converted to, and hence present as, methyl acetate in the liquid reaction composition by reaction with acetic acid product or solvent. The methyl acetate concentration in the liquid reaction composition is suitably in the range from 1 to 70% by weight, preferably from 2 to 50% by weight and more preferably from 5 to 40% by weight.

The carbon monoxide fed to the carbonylation reactor may be essentially pure or may contain inert impurities such as carbon dioxide, methane, nitrogen, noble gases, water and $C_1$ to $C_4$ paraffinic hydrocarbons. The partial pressure of carbon monoxide in the carbonylation reactor is suitably in the range from 1 to 70 bar, preferably from 1 to 35 bar, more preferably from 1 to 20 bar.

The carbonylation reactor is suitably maintained at a pressure in the range from 10 to 200 barg, preferably from 15 to 100 barg, more preferably from 15 to 50 barg.

The carbonylation reactor is suitably maintained at a temperature in the range from 100 to 300° C., preferably in the range from 150 to 220° C.

The process of the present invention is preferably performed as a continuous process but may be performed as a batch process.

The iridium catalyst in the liquid reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^- H^+$, $[Ir(CO)_2Br_2]^-H^+$, $[Ir(CO)_2I_4]^{-H+}$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$, preferably, chloride-free complexes of iridium such as acetates, oxalates and acetoacetates which are soluble in one or more of the carbonylation reaction components such as water, alcohol and/or carboxylic acid. Particularly preferred is green iridium acetate which may be used in an acetic acid or aqueous acetic acid solution. The concentration of iridium is suitably less than 2500 ppm, preferably from 400 to 2000 ppm.

In the process of the present invention optionally one or more promoters may be present in the reaction composition. Suitable promoters are preferably selected from the group consisting, of ruthenium, osmium, rhenium, cadmium, mercury, zinc, gallium, indium and tungsten, and are more preferably selected from ruthenium and osmium and most preferably is ruthenium. Preferably, the promoter is present in an effective amount up to the limit of its solubility in the liquid reaction composition aid/or any liquid process streams recycled to the carbonylation reactor from the acetic acid recovery stage. The promoter is suitably present in the liquid reaction composition at a molar ratio of promoter:iridium of [from 0.5 to 15]:1.

The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form. Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]^-H^+$, $[Ru(CO)_2I_2]_n$, $[Ru(CO)_4I_2]$, $[Ru(CO)_3I_2]_2$, tetra(aceto)chlororuthenium(II,III), ruthenium (III) acetate, ruthenium (III) propionate, ruthenium (III) butyrate, ruthenium pentacarbonyl, triruthieniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthienium(II), tetrachlorobis(benzene)diruthenium((II), dichloro(cyclooctа-1,5-diene) ruthenium (II) polymer and tris(acetylacetonate)ruthenium (III).

Examples of suitable osmium-containing compounds which may be used as sources of promoter include osmium (III) chloride hydrate and anhydrous, osmium metal, osmium tetraoxide, triosmiumdodecacarbonyl, $[Os(CO)_4I_2]$, $[Os(CO)_3I_2]_2$, $[Os(CO)_3I_3]^-H^+$, and mixed osmium halocarbonyls such as tricarbonyldichloroosmium (II) dimer and other organoosmium complexes.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.xH_2O$ $[Re(CO)_4I]_2$, $[Re(CO)_4I_2]^-H^+$ and $ReCl_5.yH_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used as sources of promoter include $Hg(OAc)_2$, $HgI_2$, $HgBr_2$, $HgCl_2$, $Hg_2I_2$, and $Hg_2Cl_2$.

Examples of suitable zinc-containing compounds which may be used as sources of promoter include $Zn(OAc)_2$, $Zn(OH)_2$, $ZnI_2$, $ZnBr_2$, $ZnCl_2$, and zinc acetylacetonate.

Examples of suitable gallium-containing compounds which may be used as sources of promoter include gallium acetylacetonate, gallium acetate, $GaCl_3$, $GaBr_3$, $GaI_3$, $Ga_2Cl_4$ and $Ga(OH)_3$.

Examples of suitable indium-containing compounds which may be used as sources of promoter include indium acetylacetonate, indium acetate, $InCl_3$, $InBr_3$, $InI_3$, $InI$ and $In(OH)_3$.

Examples of suitable tungsten-containing compounds which may be used as sources of promoter include $W(CO)_6$, $WCl_4$, $WCl_6$, $WBr_5$, $WI_2$, or $C_9H_{12}$ $W(CO)_3$.

Preferably, the iridium- and promoter-containing compounds are free of impurities which provide or generate insitu ionic iodides which may inhibit the reaction, for example, alkali or alkaline earth metal or other metal salts.

Ionic contaminants such as, for example, (a) corrosion metals, particularly nickel, iron and chromium and (b) phosphines or nitrogen-containing compounds or ligands which may quaternize in situ should be kept to a minimum in the liquid reaction composition as these may generally have an adverse effect on the reaction by generating I⁻ in the liquid reaction composition which may have an adverse effect on the reaction rate. Some corrosion metal contaminants such as for example molybdenum have been found to be less susceptible to the generation of I⁻

Corrosion metals which have an adverse affect on the reaction rate may be minimized by using suitable corrosion resistant materials of construction. Similarly, contaminants such as alkali metal iodides, for example lithium iodide, may be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4,007,130. Ionic contaminants may be kept below a concentration at which they would generate less than 500 ppm I⁻, preferably less than 250 ppm I⁻ in the liquid reaction composition.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of the reaction composition withdrawn from the carbonylation reactor and may be recycled in controlled amounts to maintain the required concentration of the water in the liquid reaction composition. Suitably, the concentration of water in the liquid reaction composition is in the range from 0.5 to 8% by weight.

In a further embodiment of the present invention, liquid reaction composition may be withdrawn from the carbonylation reactor and introduced, with or without the addition of heat to a preliminary flash zone. In this preliminary flash zone, a preliminary flash vapour fraction comprising some of the methyl acetate, methyl iodide, acetic acid, water, methanol and propionic acid precursors in the introduced liquid reaction composition, is separated from a preliminary flash liquid fraction comprising the remaining components. The preliminary flash vapour fraction is recycled to the carbonylation reactor. The preliminary flash liquid fraction is introduced to the flash zone of the present invention with or without the addition of heat, in the same way as if the preliminary flash zone had not been used. In this embodiment, the preliminary flash zone is preferably operated at a pressure below that of the reactor, typically at a pressure of 3 to 9 bara and the flash zone is operated at a pressure below that of the preliminary flash zone, typically at a pressure of 1 to 4 bara. Preferably, the preliminary flash zone is maintained at a temperature of 120 to 160° C. and the flash zone is maintained at a temperature of 100 to 140° C.

It is important that any process stream containing iridium carbonylation catalyst which is to be recycled to the carbonylation reactor contains a water concentration of at least 0.5% by weight to stabilize the iridium catalyst.

In a preferred embodiment of the present invention the reaction conditions are selected to give an acetic acid process stream from step (f) containing less than 400 ppm propionic acid and less than 1500 ppm water.

BRIEF DESCRIPTION OF THE DRAWINGS

The invention will now be illustrated by reference to the following examples and Figures in which

Referring to FIGS. 1 and 2 a carbonylation reactor (1) is provided with a stirrer (2), an inlet for carbon monoxide (3) and an inlet for methanol and/or a reactive derivative thereof (4). The reactor is also provided with an outlet (5) for withdrawing liquid reaction composition from the reactor and an outlet (6) for withdrawing gas from the head of the reactor. In FIG. 1, the outlet (5) is connected by line (7) through flashing valve (8) directly to flash zone (9).

In FIG. 2 the outlet (5) is connected by line (7) and flashing valve (27) to preliminary flash zone (28). In FIG. 2 the preliminary flash zone (28) is provided with a vapour outlet (29) for recycling to the reactor, preliminary flash zone vapour fraction comprising some of the methyl acetate, acetic acid, methyl iodide, water, methanol and propionic acid precursors in the liquid reaction composition introduced into the preliminary flash zone. This is condensed and pumped back or fed back to the reactor (1) using a pump (31). In FIG. 2 the preliminary flash zone is also provided with an outlet (30) for passing preliminary flash zone liquid comprising the remaining components of the introduced liquid reaction composition to the flash zone (9).

In FIGS. 1 and 2 the flash zone (9) is an adiabatic flash zone without heat input and is provided with an outlet (10) for a vapour fraction and an outlet (11) for a liquid fraction formed in use therein. In an alternative embodiment, heat can be supplied to the flash zone (9) to alter the ratio of vapour and liquid fractions. The flash zone is also provided with a scrubbing section (12) and optional wash through line (13). The liquid outlet (11) from the flash zone is connected to recycle pump (14) for recycling the liquid fraction to the reactor. At least part of the flash zone liquid fraction may be passed through an ion exchange resin bed (15) to remove corrosion metals therefrom and maintain the concentration of corrosion metals in the liquid reaction composition at less than that which would generate less than 500 ppm I⁻. The vapour outlet (10) from the flash zone is connected to a first distillation zone (16) provided with an overhead condenser (17) and decanter (18). In user the vapours from the distillation zone are condensed into the decanter and form two phases, a methyl iodide-rich phase and an aqueous phase. The heavy methyl iodide rich phase is recycled to the carbonylation reactor and the lighter aqueous phase is divided; part being used as reflux to the distillation zone and part being recycled to the carbonylation reactor. The distillation zone is provided with an optional methanol feed (19) to convert hydrogen iodide to methyl iodide which is returned to the carbonylation reactor from the distillation zone in the overhead recycles. The distillation zone is provided with a base liquid take-off (20) for removing a process stream comprising acetic acid containing less than 1500 ppm water and less than 400 ppm propionic acid. Alternatively, the distillation zone (16) in FIGS. 1 and 2 may be provided below the feed point with a take-off for a vapour stream comprising acetic acid product containing less than 1500 ppm water and less than 400 ppm propionic acid and with a base liquid take-off suitably for recycle to the reactor.

Figure 2:
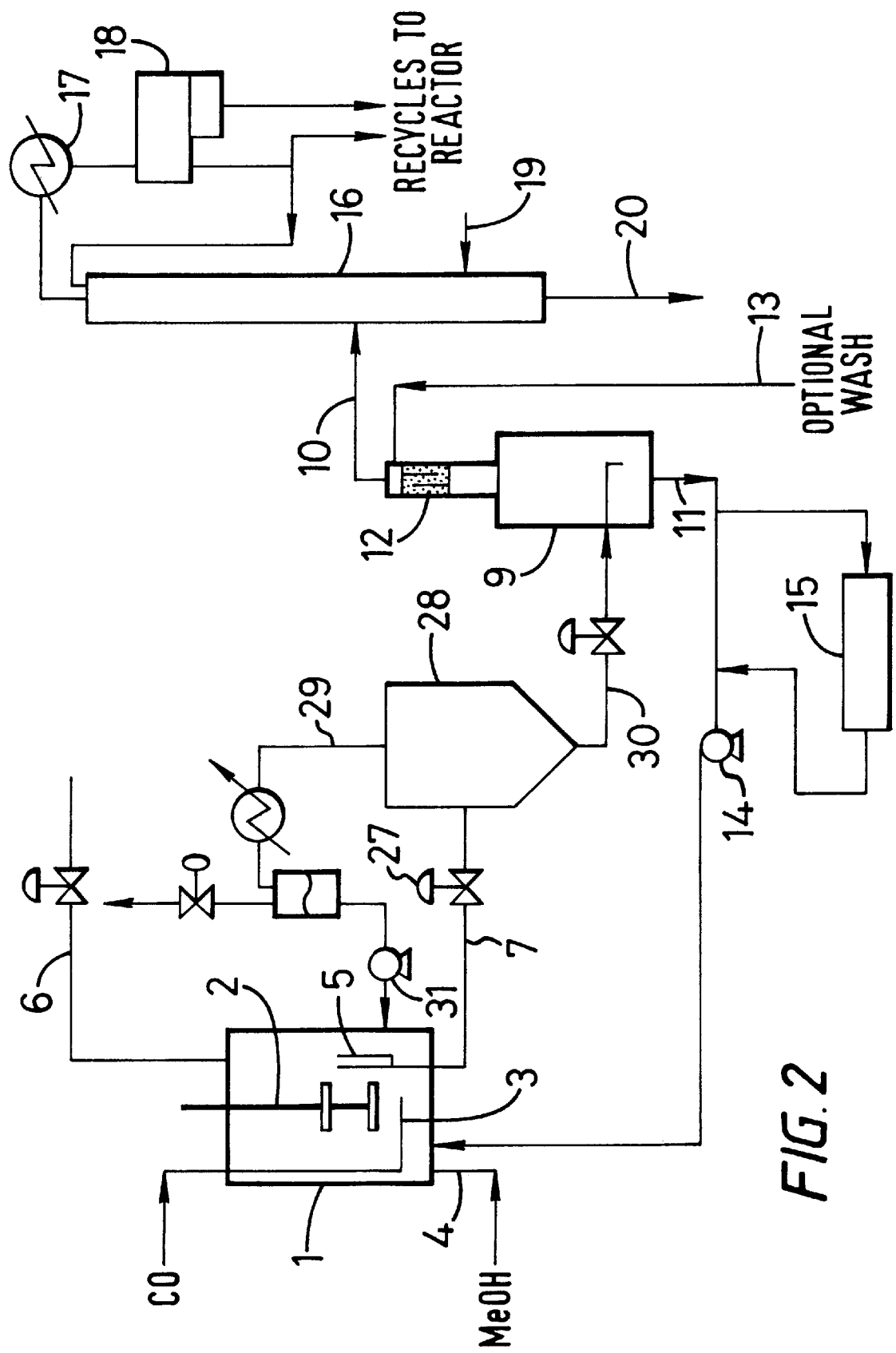
FIG. 2 represents in schematic form apparatus for performing another preferred embodiment of the process of the present invention having a preliminary flash zone and FIG. 3 represents in schematic form a further embodiment of the present invention wherein further purification with respect to propionic acid is effected.

An advantage of using a preliminary flash zone as depicted in FIG. 2 is that the decanter (18) may be dispensed with because the overhead from the distillation zone (16) will generally be single phased. Not only does this result in a capital saving but it also offers operational advantage in that it avoids any problems associated with consistently obtaining and maintaining two phases.

Figure 1:
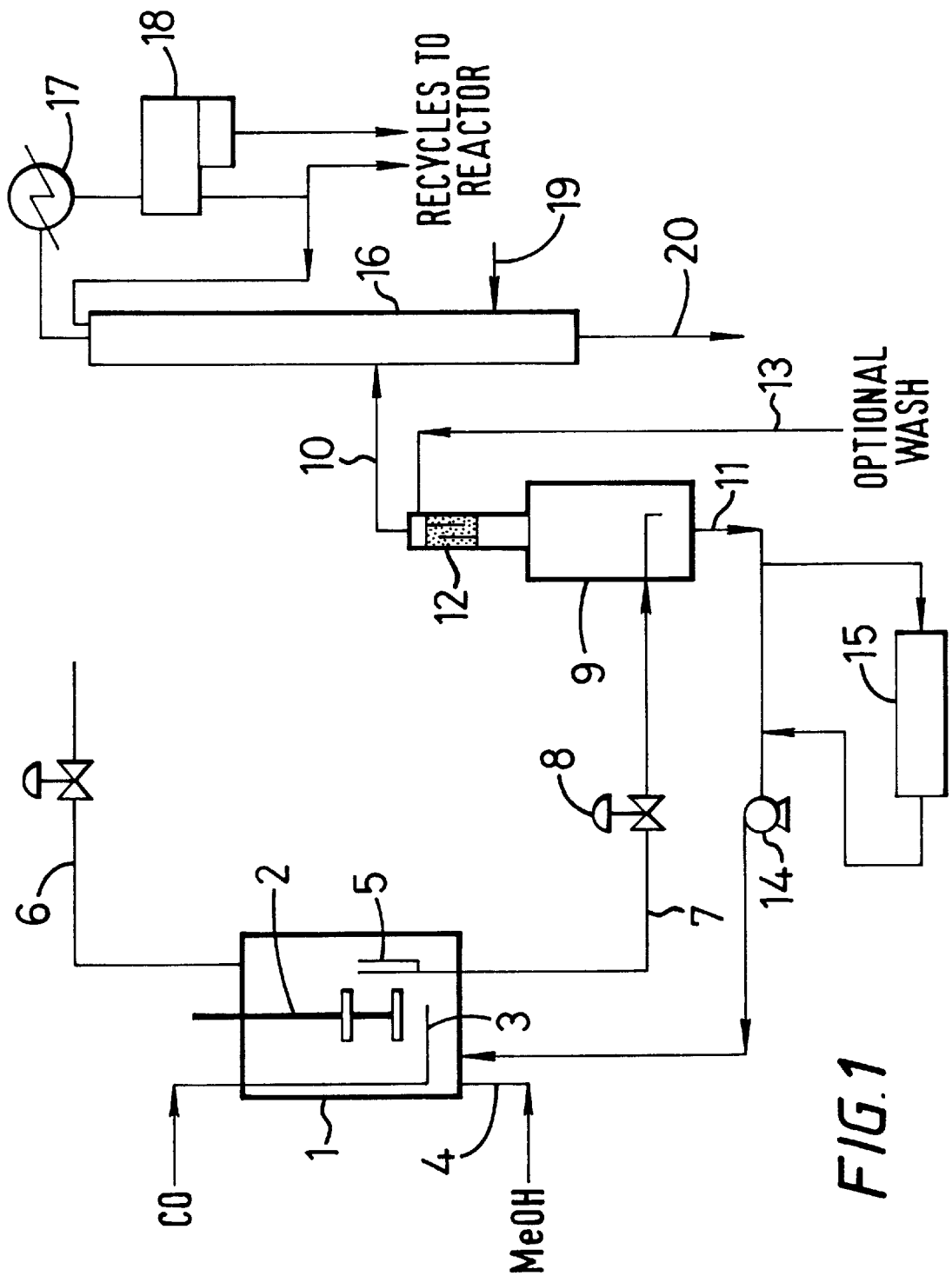
FIG. 1 represents in schematic form apparatus for performing a preferred embodiment of the process of the present invention having a single flash zone.
Figure 3:
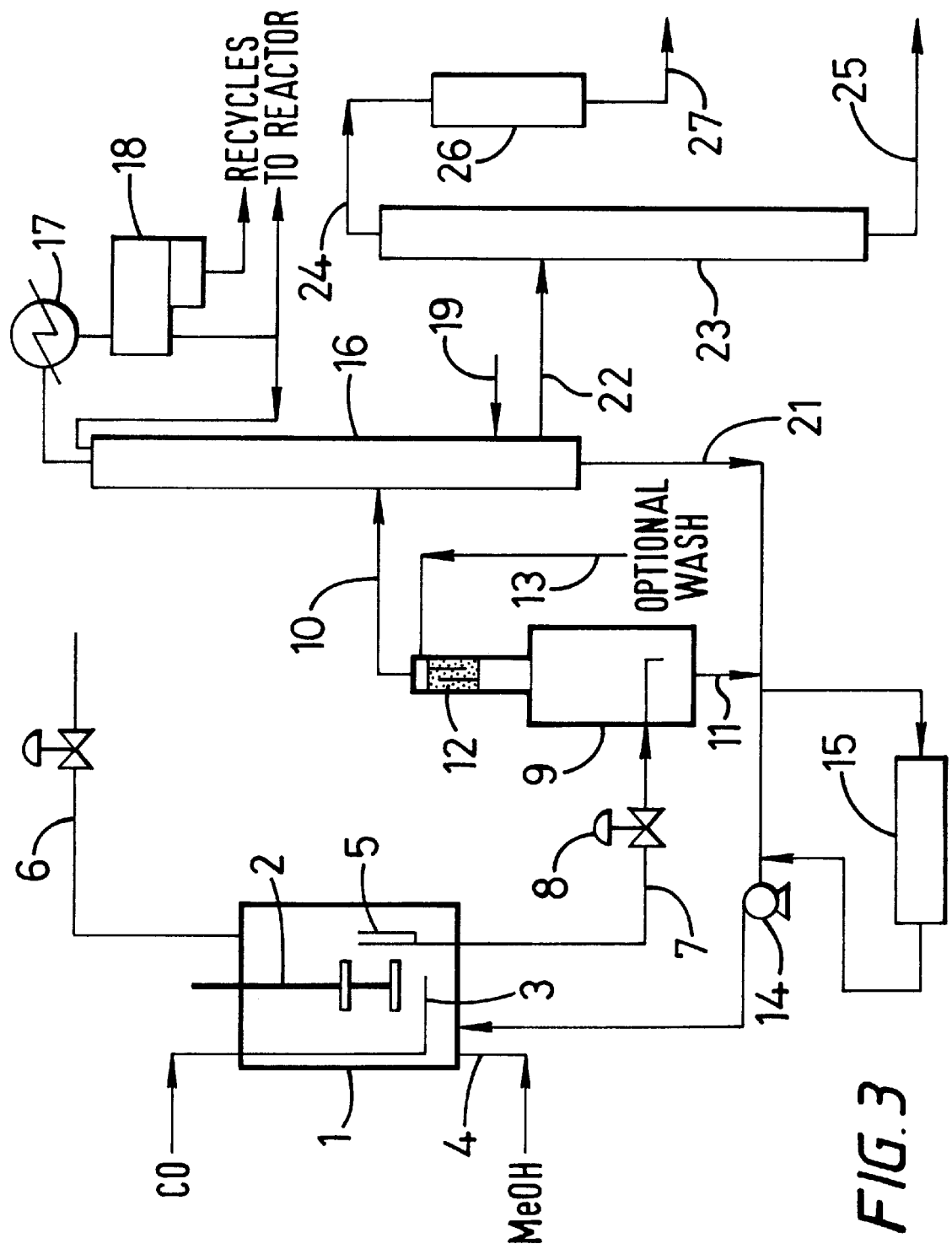

In FIG. 3, (1) to (19) are identical to FIG. 1. Thereafter the distillation zone (16) is provided with an optional base liquid bleed outlet (21) for withdrawing and recycling involatile iridium and other high-boiling impurities, if present, to the carbonylation reactor (1). The distillation zone (16) is also provided, below the feed point, with a take-off (22) for a vapour process stream comprising acetic acid product and propionic acid by-product. From the vapour process stream take-off (22) the vapour is fed to an intermediate point in a second distillation column (23) which is provided with a head take-off (24) for acetic acid containing less than 1500 ppm water and less than 400 ppm propionic acid. Alternatively, acetic acid containing less than 1500 ppm water and less than 400 ppm propionic acid may be taken off the second distillation column (23) as a side-draw above the vapour feed point, with recycle of at least a part of the heads take-off after condensation thereof, either to the reactor (1) and/or the first distillation column (16). This alternative is not shown in FIG. 3.

The second distillation column (23) is provided with a base take-off (25) for by-product propionic acid removal.

The process conditions used in the carbonylation reactor (1) may typically be:

| | |
|---|---|
| temperature | 181 to 195° C.; |
| total pressure | 22 to 32 bar gauge; |
| carbon monoxide partial pressure | 8 to 10 bar; |
| hydrogen partial pressure | 0.05 to 0.3 bar; and |
| liquid reaction composition component concentrations: - | |
| iridium | 700 to 1500 ppm; |
| ruthenium | 1500 to 2500 ppm; |
| methyl acetate | 10 to 25% by weight; |
| methyl iodide | 6 to 12% by weight |
| water | 3 to 8% by weight. |

In the apparatus shown in FIG. 1, the flash zone and distillation zone may be operated at a pressure of 1 to 3 bar gauge. In the apparatus shown in FIG. 2, the preliminary flash zone (28) is operated at a higher pressure (for example 2 to 8 bar gauge) than the flash zone (9) and first distillation zone which may be operated at a pressure of 0 to 3 bar gauge.

EXAMPLES 1–5

The apparatus illustrated in FIG. 1 was used to produce acetic acid employing the conditions shown in the following Table.

TABLE

| | Ex 1 | Ex 2 | Ex 3 | Ex 4 | Ex 5 |
|---|---|---|---|---|---|
| Reactor conditions | | | | | |
| Reactor Temperature (° C.) | 189.0 | 191.2 | 189.0 | 189.0 | 189.0 |
| Reactor Pressure | 27.4 | 27.6 | 29.9 | 30.0 | 29.6 |
| CO partial pressure (bar) | 8.1 | 8.9 | 9.1 | 8.8 | 8.3 |
| $H_2$ partial pressure (bar) | 0.18 | 0.21 | 0.18 | 0.15 | 0.12 |
| Liquid reaction composition | | | | | |
| Water (% by weight) | 7.8 | 4.7 | 5.1 | 4.6 | 5.7 |
| Methyl iodide (% by weight) | 7.1 | 6.6 | 9.6 | 10.0 | 10.3 |
| Methyl acetate | 18.2 | 14.3 | 19.8 | 21.9 | 22.3 |

TABLE-continued

| | Ex 1 | Ex 2 | Ex 3 | Ex 4 | Ex 5 |
|---|---|---|---|---|---|
| (% by weight) | | | | | |
| Ir (ppm) | 1320 | 1170 | 930 | 840 | 870 |
| Ru (ppm) | 1760 | 1610 | 2040 | 2330 | 2870 |
| $H_2$ in feed (% v/v) | 0.86 | 0.06 | 0.30 | 0.30 | 0.29 |
| Carbonylation rate (mol/l/hr) | 17.8 | 17.3 | 20.3 | 19.8 | 19.8 |
| $CO_2$ rate (% of carbonylation rate) | 0.88 | 0.98 | 0.68 | 0.63 | 0.67 |
| $CH_4$ rate (% of carbonylation rate) | 1.02 | 0.83 | 0.89 | 0.81 | 0.84 |
| Process stream from step (f) | | | | | |
| Water in process stream (20) | 510 | 780 | 790 | 920 | 930 |
| Propionic acid in process stream (20) | 380 | 390 | 390 | 360 | 290 |

What is claimed is:

1. A process for the production of an acetic acid process stream comprising less than 400 ppm propionic acid and less than 1500 ppm water which process comprises the steps of:
   (a) feeding methanol and/or a reactive derivative thereof and carbon monoxide to a carbonylation reactor in which there is maintained during the course of the process a liquid reaction composition comprising:
      (i) an iridium carbonylation catalyst;
      (ii) methyl iodide co-catalyst;
      (iii) one or more promoters selected from the group consisting of ruthenium, osmium, rhenium, cadmium, mercury, zinc, gallium, indium and tungsten present in the liquid reaction composition at a molar ratio of promoter: iridium of from 0.5 to 15:1;
      (iv) a finite amount of water at a concentration of less than about 8% by weight;
      (v) methyl acetate;
      (vi) acetic acid; and
      (vii) propionic acid by-product and its precursors;
      and in which composition ionic contaminants are kept below a concentration at which they would generate less than 500 ppm $I^-$:
   (b) withdrawing liquid reaction composition from the carbonylation reactor and introducing at least part of the withdrawn liquid reaction composition, with or without the addition of heat, to a flash zone to form a vapor fraction comprising water, acetic acid product, propionic acid by-product, methyl acetate, methyl iodide and propionic acid precursors, and a liquid fraction comprising involatile iridium catalyst, involatile promoter or promoters, acetic acid and water;
   (c) recycling the liquid fraction from the flash zone to the carbonylation reactor;
   (d) introducing the vapor fraction from the flash zone into a first distillation zone;
   (e) removing from the first distillation zone at a point above the introduction point of the flash zone vapor fraction a light ends recycle stream comprising water, methyl acetate, methyl iodide, acetic acid and propionic acid precursors which stream is recycled in whole or in part to the carbonylation reactor, and
   (f) removing from the first distillation zone at a point below the introduction point of the flash zone vapor fraction, a process stream comprising acetic acid product, greater than 400 ppm propionic acid by-product, and less than 1500 ppm water and, (g) introducing said stream into a second distillation column, removing from a point below the introduction point of the stream from (f) propionic acid by-product and from a point above the introduction point of the stream from (f) an acetic acid process stream containing less than 400 ppm propionic acid and less than 1500 ppm water.

2. A process according to claim 1 wherein methanol and/or methyl acetate is (are) fed to the carbonylation reactor.

3. A process according to claim 1 wherein the concentration of methyl iodide co-catalyst in the liquid reaction composition is from 4 to 16% by weight.

4. A process according to claim 1 wherein the methyl acetate concentration in the liquid reaction composition is in the range from 5 to 40% by weight.

5. A process according to claim 1 wherein the concentration of water in the liquid reaction composition is in the range from 0.5 to 8% by weight.

6. A process according to claim 1 wherein the concentration of iridium catalyst in the liquid reaction composition is from 400 to 2000 ppm.

7. A process according to claim 1 wherein the molar ratio of methyl iodide:iridium in the liquid reaction composition is from 20 to 200:1.

8. A process according to claim 1 wherein hydrogen present in the carbonylation reactor is maintained at a partial pressure less than 0.3 bar.

9. A process according to claim 1 wherein hydrogen in the carbon monoxide feed gas is maintained at less than 0.3 mol %.

10. A process according to claim 1 wherein the promoter is ruthenium.

11. A process according to claim 1 wherein the carbonylation temperature is in the range from 150 to 220° C. and the carbonylation pressure is in the range from 15 to 50 barg.

12. A process according to claim 1 wherein in the liquid reaction composition methyl acetate is present in an amount from 10 to 25% by weight, methyl iodide is present in an amount from 6 to 12% by weight, water is present in an amount from 3 to 8% by weight, iridium is present in an amount of from 700 to 1500 ppm, ruthenium is present in an amount of from 1500 to 2500 ppm, the carbon monoxide partial pressure is from 8 to 10 bar, the hydrogen partial pressure is from 0.05 to 0.3 bar, the carbonylation temperature is from 181 to 195° C. and the carbonylation total pressure is from 22 to 32 barg.

13. A process according to claim 1 wherein the first distillation zone has up to 40 theoretical stages.

14. A process according to claim 1 wherein liquid reaction composition is withdrawn from the carbonylation reactor and introduced with or without the addition of heat to a preliminary flash zone in which a preliminary flash vapour fraction comprising some of the methyl acetate, methyl iodide, acetic acid, water, methanol and propionic acid precursors in the introduced liquid reaction composition is separated from a preliminary flash liquid fraction comprising the remaining components, the preliminary flash vapour fraction is recycled to the carbonylation reactor and the preliminary flash liquid fraction is introduced to the flash zone of step (b).

15. A process as claimed in claim 1 wherein the process stream removed in step (f) is removed as a vapor.

16. A process as claimed in claim 1 wherein the process stream removed in step (f) is removed as a liquid.

* * * * *